US012740521B2

(12) United States Patent
Mai et al.

(10) Patent No.: US 12,740,521 B2
(45) Date of Patent: Sep. 22, 2026

(54) TISSUE CULTURE METHOD AND PROPAGATION METHOD OF *CATHAYA ARGYROPHYLLA*

(71) Applicant: GX ECO-ENGINEERING VOCATIONAL & TECHNICAL COLLEGE, Liuzhou City (CN)

(72) Inventors: Kaile Mai, Liuzhou City (CN); Rongzhen Li, Liuzhou City (CN); Changsan Zhu, Liuzhou City (CN); Lixin Feng, Liuzhou City (CN); Yuanchang Lu, Liuzhou City (CN); Xianzhao Liu, Liuzhou City (CN); Jienan Su, Liuzhou City (CN); Jianhua Lan, Liuzhou City (CN); Debao Liao, Liuzhou City (CN); Kun Qin, Liuzhou City (CN)

(73) Assignee: GX ECO-ENGINEERING VOCATIONAL & TECHNICAL COLLEGE, Liuzhou City (CN)

( * ) Notice: Subject to any disclaimer, the term of this patent is extended or adjusted under 35 U.S.C. 154(b) by 616 days.

(21) Appl. No.: 18/209,503

(22) Filed: Jun. 14, 2023

(65) Prior Publication Data

US 2023/0404005 A1 Dec. 21, 2023

(30) Foreign Application Priority Data

Jun. 14, 2022 (CN) ......................... 202210668133.0

(51) Int. Cl.
*A01H 4/00* (2006.01)

(52) U.S. Cl.
CPC ............. *A01H 4/008* (2013.01); *A01H 4/002* (2021.01)

(58) Field of Classification Search
CPC ................................ A01H 4/008; A01H 4/002
See application file for complete search history.

(56) References Cited

FOREIGN PATENT DOCUMENTS

CN 109479712 B * 9/2020 ............ A01H 4/008

OTHER PUBLICATIONS

Perez-Bermudez et al. (1987), Factors affecting adventitious bud induction in *Pinus elliottii* (Engelm.) embryos cultured in vitro. Plant Cell. 11:25-35 (Year: 1987).*

PhytoTechnology Laboratories®. (2014). Technical Information: Agars & Other Gelling Agents. p. 1-4. (Year: 2014).*

Rahman, M., et al. (2018) Effect of Auxin (NAA, IBA and IAA) in Root Regeneration through In vitro Culture of Sugarcane. Int J Plant Biol Res 6(6): 1109. (Year: 2018).*

Sun et al. (2006). Formation of Mycorrhiza-like Structures in Cultured Root/Callus of Cathaya argyrophylla Chun et Kuang Infected with the Ectomycorrhizal Fungus Cenococcum geophilum Fr. Journal of Integrative Plant Biology vol. 48. (Year: 2006).*

Canavera, D., (1978). Effects of various growing media on container-grown yellow birch. Tree Planters' Notes: A Publication for Nurserymen and Planters of Forests and Shelterbelts, vols. 29-33, p. 13. (Year: 1978).*

McKeand et al. (1985). Expression of Mature Characteristics by Tissue Culture Plantlets Derived from Embryos of Loblolly Pine. J. Amer. Soc. Hort. Sci. 110(5):619-623. (Year: 1985).*

* cited by examiner

*Primary Examiner* — Bratislav Stankovic
*Assistant Examiner* — Emily K Johnson
(74) *Attorney, Agent, or Firm* — Edell, Shapiro & Finnan, LLC

(57) ABSTRACT

A tissue culture method and a propagation method of *Cathaya argyrophylla* are described herein. An adventitious bud can be induced from an explant of the *Cathaya argyrophylla* using a suitable induction medium, with an induction rate reaching 69.22% to 73.33%. The induced adventitious bud is inoculated into a suitable proliferation medium, such that the adventitious bud can proliferate and strengthen seedlings, where the adventitious bud shows a proliferation rate reaching 46.23% to 55%. The adventitious bud after proliferation and seedling strengthening are inoculated into a suitable rooting medium to allow rooting culture, thereby obtaining a complete tissue culture seedling of the *Cathaya argyrophylla*. The tissue culture method is of great significance for protecting the *Cathaya argyrophylla*, increasing a plant quantity of the *Cathaya argyrophylla*, and expanding a population of the *Cathaya argyrophylla* to prevent extinction.

10 Claims, No Drawings

TISSUE CULTURE METHOD AND PROPAGATION METHOD OF *CATHAYA ARGYROPHYLLA*

CROSS REFERENCE TO RELATED APPLICATION

This patent application claims the benefit and priority of Chinese Patent Application No. 202210668133.0, filed with the China National Intellectual Property Administration on Jun. 14, 2022, the disclosure of which is incorporated by reference herein in its entirety as part of the present application.

TECHNICAL FIELD

The present disclosure relates to the technical field of plant tissue culture, in particular to a tissue culture method and a propagation method of *Cathaya argyrophylla*.

BACKGROUND

*Cathaya argyrophylla* Chun et Kuang is a single genus of Pinaceae, and a unique relic plant in China. The *Cathaya argyrophylla* is a rare and endangered plant protected at the national first level, and has been included in the list of plant species with extremely small populations. *Cathaya argyrophylla*, as a precious ornamental tree species, is evergreen in all seasons. This tree species has a beautiful tree body, tall and majestic trunk, and highly ornamental silver bands on its leaf back.

The ancient origin of *Cathaya argyrophylla* shows important scientific reference values for the phylogeny and evolution of *Pinus*, as well as the research of paleontology, paleoclimatology, paleogeology, and paleoecology.

*Cathaya argyrophylla* populations have difficulty in regeneration and are lack of seedlings. Compared with other Pinaceae plants, although the immature embryos of *Cathaya argyrophylla* have less number than those of *Pinus* at an early stage of development and show later fission, a whole process of embryo development for the immature embryos of *Cathaya argyrophylla* is highly close to that of the *Pinus*. *Cathaya argyrophylla* has a small amount of seeds and a low proportion of viable seeds, and both seeds and seedlings are susceptible to diseases. The *Cathaya argyrophylla* shows difficulty in sexual reproduction, and has a poor survival rate in seedlings. Natural *Cathaya argyrophylla* has extremely slow growth of seedlings and high mortality of seedlings and saplings, which seriously restricts the natural regeneration of *Cathaya argyrophylla* populations. Asexual reproduction is one of the feasible ways to obtain asexual seedlings of *Cathaya argyrophylla* and to construct germplasm resources.

The research on tissue culture seedlings of *Cathaya argyrophylla* mainly focuses on direct organogenesis. For example, scholars use branches, cotyledons, and hypocotyls of *Cathaya argyrophylla* prepared by culture in vitro as raw materials to conduct induction with growth regulators such as 6-BA, NAA, and 2,4-D in media such as White, 1/2MS, and WPS, thereby obtaining callus. Scholars also used mature embryos and hypocotyls of *Cathaya argyrophylla* to induce a small amount of adventitious buds on a modified Monnier medium, but these adventitious buds cannot elongate to further form plants. A tissue culture-derived regenerated plant system of the *Cathaya argyrophylla* cannot be established.

At present, it is urgent to protect the *Cathaya argyrophylla*, increase the number of *Cathaya argyrophylla* plants, and expand the population of *Cathaya argyrophylla* to prevent extinction. In view of this, it is one of the important ways to solve this problem by conducting the in vitro culture of *Cathaya argyrophylla*, cultivating the clone plants of *Cathaya argyrophylla*, cultivating the regenerated plants of *Cathaya argyrophylla*, and establishing a regeneration system of the clone plants of *Cathaya argyrophylla*.

SUMMARY

In order to solve the above problems, the present disclosure provides a tissue culture method of *Cathaya argyrophylla*. In the present disclosure, the tissue culture method can not only improve an induction rate of adventitious buds, but also make the adventitious buds proliferate and differentiate into adventitious roots, so as to obtain tissue culture seedlings of the *Cathaya argyrophylla*.

To achieve the above objective, the present disclosure provides the following technical solutions:

The present disclosure provides a tissue culture method of *Cathaya argyrophylla*, including the following steps:

- inoculating an explant of the *Cathaya argyrophylla* into an induction medium to allow induction culture to obtain an adventitious bud of the *Cathaya argyrophylla*; where
- the induction medium includes a basic medium and 1.5 mg/L of 6-benzyladenine (6-BA); and the basic medium of the induction culture is selected from the group consisting of a DCR medium and a P6 medium;
- inoculating the adventitious bud of the *Cathaya argyrophylla* into a proliferation medium to allow proliferation culture to obtain a proliferated adventitious bud; where
- the proliferation medium uses the DCR medium as a basic medium, and further includes 0.5 mg/L to 1.5 mg/L of the 6-BA and 0.2 mg/L to 0.6 mg/L of 1-naphthylacetic acid (NAA); and
- inoculating the proliferated adventitious bud into a rooting medium to allow rooting culture to obtain a tissue culture seedling; where
- the rooting medium uses a 1/2MS medium as a basic medium, and further includes 0.5 mg/L of indole-3-butyric acid (IBA) and 0.2 mg/L of the NAA.

Preferably, the explant includes a zygotic embryo.

Preferably, the explant is derived from *Cathaya argyrophylla* in Jinxiu Yao Autonomous County of Guangxi or Huaping Town in Guilin;

- when the explant is derived from the *Cathaya argyrophylla* in the Jinxiu Yao Autonomous County of Guangxi, the basic medium of the induction medium is the DCR medium; and
- when the explant is derived from the *Cathaya argyrophylla* in the Huaping Town in Guilin, the basic medium of the induction medium is the P6 medium.

Preferably, when the explant is derived from the *Cathaya argyrophylla* in the Jinxiu Yao Autonomous County of Guangxi, the proliferation medium uses the DCR medium as a basic medium, and further includes 0.5 mg/L of the 6-BA and 0.2 mg/L of the NAA; alternatively, the proliferation medium uses the DCR medium as a basic medium, and further includes 1.5 mg/L of the 6-BA and 0.6 mg/L of the NAA; and

- when the explant is derived from the *Cathaya argyrophylla* in the Huaping Town in Guilin, the proliferation medium uses the DCR medium as a basic medium, and further includes 1 mg/L of the 6-BA and 0.4 mg/L of the NAA.

Preferably, the induction medium, the proliferation medium, and the rooting medium each further include the following components in mass percentage: 3% of sucrose and 4.5‰ of agar.

Preferably, the induction medium, the proliferation medium, and the rooting medium each have a pH value of 5.6 to 5.8.

Preferably, the induction culture, the proliferation culture, and the rooting culture are independently conducted by: a culture temperature of 23° C. to 27° C., a daily illumination time of 12 h to 14 h, a light intensity of 2,000 1× to 3,000 1×, and a relative humidity of 60% to 80%.

Preferably, the induction culture is conducted for 10 weeks; the proliferation culture is conducted for 12 weeks; and the rooting culture is conducted for 8 weeks.

The present disclosure further provides a propagation method of *Cathaya argyrophylla*, including the following steps: preparing a tissue culture seedling by the tissue culture method; and subjecting the tissue culture seedling to transplanting culture to obtain a *Cathaya argyrophylla* seedling.

Preferably, a culture substrate of the transplanting culture includes peat and perlite; and the peat and the perlite in the culture substrate are at a volume ratio of 4:1.

The present disclosure has the following beneficial effects:

The present disclosure provides a tissue culture method of *Cathaya argyrophylla*, including the following steps: inoculating an explant of the *Cathaya argyrophylla* into an induction medium to allow induction culture to obtain an adventitious bud of the *Cathaya argyrophylla*; where the induction medium includes a basic medium and 1.5 mg/L of 6-BA; and the basic medium of the induction culture is selected from the group consisting of a DCR medium and a P6 medium; inoculating the adventitious bud of the *Cathaya argyrophylla* into a proliferation medium to allow proliferation culture to obtain a proliferated cell line; where the proliferation medium uses the DCR medium as a basic medium, and further includes 0.5 mg/L to 1.5 mg/L of the 6-BA and 0.2 mg/L to 0.6 mg/L of NAA; and inoculating the proliferated adventitious bud into a rooting medium to allow rooting culture to obtain a tissue culture seedling; where the rooting medium uses a 1/2MS medium as a basic medium, and further includes 0.5 mg/L of IBA and 0.2 mg/L of the NAA.

Compared with the prior art, the present disclosure has the following advantages:

(1) In the present disclosure, adventitious buds can be induced from the explant of *Cathaya argyrophylla* using a suitable induction medium, and the adventitious buds can be proliferated and differentiated to obtain a proliferated cell line. The tissue culture method has high induction rate and proliferation rate of adventitious buds, and can effectively obtain complete tissue culture seedlings of the *Cathaya argyrophylla.*

(2) In the present disclosure, the tissue culture method can effectively increase a plant quantity of *Cathaya argyrophylla*, expand a population of *Cathaya argyrophylla*, and realize the protection against extinction of *Cathaya argyrophylla.*

DETAILED DESCRIPTION OF THE EMBODIMENTS

The present disclosure provides a tissue culture method of *Cathaya argyrophylla*, including the following steps:

inoculating an explant of the *Cathaya argyrophylla* into an induction medium to allow induction culture to obtain an adventitious bud of the *Cathaya argyrophylla*; where the induction medium includes a basic medium and 1.5 mg/L of 6-benzyladenine (6-BA); and the basic medium of the induction culture is selected from the group consisting of a DCR medium and a P6 medium;

inoculating the adventitious bud of the *Cathaya argyrophylla* into a proliferation medium to allow proliferation culture to obtain a proliferated cell line; where the proliferation medium uses the DCR medium as a basic medium, and further includes mg/L to 1.5 mg/L of the 6-BA and 0.2 mg/L to 0.6 mg/L of 1-naphthylacetic acid (NAA); and inoculating the proliferated cell line into a rooting medium to allow rooting culture to obtain a tissue culture seedling; where the rooting medium uses a 1/2MS medium as a basic medium, and further includes 0.5 mg/L of indole-3-butyric acid (IBA) and 0.2 mg/L of the NAA.

Unless otherwise specified, the present disclosure has no special requirements for sources of the basic medium, and commercially-available products well known to those skilled in the art may be adopted.

In the present disclosure, an explant of the *Cathaya argyrophylla* is inoculated into an induction medium to allow induction culture to obtain an adventitious bud of the *Cathaya argyrophylla*. The explant includes preferably a zygotic embryo, more preferably a mature zygotic embryo.

In the present disclosure, a preparation method of the zygotic embryo includes preferably the following steps:

step I: peeling off seeds from cones of *Cathaya argyrophylla*, rinsing with water, sterilizing seed coat with a 0.1% $KMnO_4$ solution, and peeling off the seed coat on an ultra-clean workbench to obtain peeled seeds;

step II: mixing the peeled seeds with 70% alcohol for 30 s, sterilizing with 0.1% mercuric chloride, and rinsing with sterile water 4 to 5 times to obtain sterilized peeled seeds; and step III: removing seed embryos from the sterilized peeled seeds with a scalpel under aseptic conditions to obtain the zygotic embryo.

In the present disclosure, the sterilization of the seed coat is conducted for preferably 20 min to 30 min, more preferably 23 min to 27 min, more preferably 25 min; and the sterilization by the 0.1% mercuric chloride is conducted for preferably 5 min to 6 min, more preferably 6 min. Sterilizing the seed coat and then the peeled seeds can make the test explant more fully sterilized to reduce contamination of the explant. In this way, a pollution rate of the explant is reduced while reducing damages to the explant, such that an effect of increasing an induced growth rate and a survival rate of the explant can be achieved.

In the present disclosure, the explant is preferably derived from *Cathaya argyrophylla* in Jinxiu Yao Autonomous County of Guangxi or Huaping Town in Guilin;

when the explant is derived from *Cathaya argyrophylla* in Jinxiu Yao Autonomous County of Guangxi, the induction medium uses preferably the DCR medium as a basic medium, and further includes the following components: 6-BA 1.5 mg/L, sucrose 3 wt. %, and agar 4.5 wt. ‰; and the induction medium has a pH value of preferably 5.6 to 5.8; and when the explant is derived from *Cathaya argyrophylla* in Huaping Town in Guilin, the induction medium uses preferably the P6 medium as a basic medium, and further includes the following components: 6-BA 1.5 mg/L, sucrose 3%, and Agar 4.5‰; and the induction medium has a pH value of preferably 5.6 to 5.8.

In the present disclosure, the induction medium is preferably subjected to high-temperature sterilization at preferably 121° C. before inoculation of the zygotic embryo.

In the present disclosure, the induction culture is conducted by: a culture temperature of preferably 23° C. to 27° C., more preferably 25° C., a daily illumination time of preferably 12 h to 14 h, more preferably 13 h, a light intensity of preferably 2,000 1× to 3,000 1×, more preferably 2,300 1× to 2,700 1×, more preferably 2,500 1×, and a relative humidity of preferably 60% to 80%, more preferably 65% to 75%, more preferably 70%.

In the present disclosure, the induction culture is preferably conducted for 10 weeks.

In the present disclosure, by culturing the explant of *Cathaya argyrophylla* in a suitable induction medium, adventitious buds can be induced from the explant of *Cathaya argyrophylla*, with an induction rate of 69.22% to 73.33%.

In the present disclosure, the adventitious bud of the *Cathaya argyrophylla* is inoculated into a proliferation medium to allow proliferation culture to obtain a proliferated cell line; where the proliferation medium uses the DCR medium as a basic medium, and further includes 0.5 mg/L to 1.5 mg/L of the 6-BA and 0.2 mg/L to 0.6 mg/L of NAA.

In the present disclosure, when the explant is derived from *Cathaya argyrophylla* in Jinxiu Yao Autonomous County of Guangxi, the proliferation medium preferably uses the DCR medium as a basic medium, and further includes 6-BA, NAA, sucrose 3 wt. %, and agar 4.5 wt. ‰; the 6-BA has a concentration of preferably 0.5 mg/L or 1.5 mg/L, more preferably 0.5 mg/L; the NAA has a concentration of preferably 0.2 mg/L or 0.6 mg/L, more preferably 0.2 mg/L; and the proliferation medium has a pH value of preferably 5.6 to 5.8.

In the present disclosure, when the explant is derived from *Cathaya argyrophylla* in Huaping Town in Guilin, the proliferation medium preferably uses the DCR medium as a basic medium, and further includes 6-BA 1 mg/L, NAA 0.4 mg/L, sucrose 3 wt. %, and agar 4.5 wt. ‰; and the proliferation medium has a pH value of preferably 5.6 to 5.8.

In the present disclosure, the proliferation medium is preferably subjected to high-temperature sterilization at preferably 121° C. before inoculation of the adventitious bud of *Cathaya argyrophylla*.

In the present disclosure, the proliferation culture is conducted by: a culture temperature of preferably 23° C. to 27° C., more preferably 25° C., a daily illumination time of preferably 12 h to 14 h, more preferably 13 h, a light intensity of preferably 2,000 1× to 3,000 1×, more preferably 2,300 1× to 2,700 1×, more preferably 2,500 1×, and a relative humidity of preferably 60% to 80%, more preferably 65% to 75%, more preferably 70%.

In the present disclosure, the proliferation culture is preferably conducted for 12 weeks.

In the present disclosure, the proliferated cell line is inoculated into a rooting medium to allow rooting culture to obtain a tissue culture seedling; where the rooting medium uses a 1/2MS medium as a basic medium, and further includes 0.5 mg/L of IBA and 0.2 mg/L of the NAA.

In the present disclosure, the proliferated cell line is preferably subjected to pre-culture before being inoculated into the rooting medium. The pre-culture includes preferably: inoculating the proliferated cell line into a pre-culture medium to allow culture for 3 weeks, and then transferring to the 1/2MS medium to allow culture for 4 weeks; where the pre-culture medium preferably uses the 1/2MS medium as a basic medium, and further includes 0.1 wt. % of biochar. The pre-culture medium can promote the development of root primordia, such that the root primordia can grow into adventitious roots in the rooting medium.

In the present disclosure, in addition to the above components, the rooting medium further includes preferably 3 wt. % of sucrose and 4.5 wt. ‰ of agar; and the rooting medium has a pH value of preferably 5.6 to 5.8.

In the present disclosure, the rooting medium is preferably subjected to high-temperature sterilization at preferably 121° C. before inoculation of the proliferated cell line.

In the present disclosure, the rooting culture or pre-culture is conducted by: a culture temperature of preferably 23° C. to 27° C., more preferably 25° C., a daily illumination time of preferably 12 h to 14 h, more preferably 13 h, a light intensity of preferably 2,000 1× to 3,000 1×, more preferably 2,300 1× to 2,700 1×, more preferably 2,500 1×, and a relative humidity of preferably 60% to 80%, more preferably 65% to 75%, more preferably 70%.

In the present disclosure, the rooting culture is preferably conducted for 8 weeks.

The present disclosure further provides a propagation method of *Cathaya argyrophylla*, including the following steps: preparing a tissue culture seedling by the tissue culture method; and subjecting the tissue culture seedling to transplanting culture to obtain a *Cathaya argyrophylla* seedling.

In the present disclosure, the tissue culture seedling is preferably subjected to domestication before the transplanting culture; and the domestication is conducted preferably by: a culture temperature of preferably 23° C. to 27° C., more preferably 25° C., a daily illumination time of preferably 12 h to 14 h, more preferably 13 h, a light intensity of preferably 2,000 1× to 3,000 1×, more preferably 2,300 1× to 2,700 1×, more preferably 2,500 1×, and a relative humidity of preferably 60% to 80%, more preferably 65% to 75%, more preferably 70%. In the present disclosure, the domestication is conducted for preferably 2 weeks.

In the present disclosure, a culture substrate of the transplanting culture includes preferably peat and perlite; and the peat and the perlite in the culture substrate are at a volume ratio of preferably 4:1. A suitable culture substrate can make the tissue culture seedlings grow normally and avoid root rot.

In order to further illustrate the present disclosure, the tissue culture method and the propagation method of *Cathaya argyrophylla* provided by the present disclosure are described in detail below in connection with examples, but these examples should not be understood as limiting the claimed scope of the present disclosure.

Example 1

A tissue culture method of *Cathaya argyrophylla* included the following steps:

1) Acquisition of an Explant

The seeds were peeled off from cones of *Cathaya argyrophylla*, rinsed with tap water, seed coat was sterilized with a 0.1% $KMnO_4$ solution for 25 min, and the seed coat was peeled off on an ultra-clean workbench to obtain peeled seeds; the peeled seeds were put into 70% alcohol for 30 s, sterilized in 0.1% mercuric chloride for 6 min, rinsed 5 times with sterile water, and a seed embryo was taken out from the peeled seeds with a scalpel under aseptic conditions to obtain a zygotic embryo.

2) Induction Culture of an Adventitious Bud

The zygotic embryo was inoculated into an induction medium to allow induction culture at 25° C., a daily illumination time of 13 h, a light intensity of 2,500 1×, and a relative humidity of 70% for 10 weeks to obtain an adventitious bud of the *Cathaya argyrophylla*; where the induction medium used a DCR medium as a basic medium, and only included the following components: 6-BA 1.5 mg/L, sucrose 3%, and agar 4.5‰; and the induction medium had a pH value of 5.7.

3) Proliferation Culture

The adventitious bud of the *Cathaya argyrophylla* was inoculated into a proliferation medium to allow proliferation culture at 23° C. to 27° C., a daily illumination time of 13 h, a light intensity of 2,500 1×, and a relative humidity of 70% for 12 weeks to obtain a proliferated cell line; where the proliferation medium used the DCR medium as a basic medium, and only included the following components: 6-BA 0.5 mg/L, NAA 0.2 mg/L, sucrose 3%, and agar 4.5‰; and the proliferation medium had a pH value of 5.7.

4) Rooting Culture

The proliferated cell line was inoculated into a pre-culture medium to allow pre-culture for 3 weeks, transferred to a 1/2MS medium to allow culture for 4 weeks, and transferred into a rooting medium to allow rooting culture for 8 weeks to obtain a tissue culture seedling; where the pre-culture and the rooting culture were conducted by: at 23° C. to 27° C., a daily illumination time of 13 h, a light intensity of 2,500 1×, and a relative humidity of 70%; the rooting medium used the 1/2MS medium as a basic medium, and only included the following components: IBA 0.5 mg/L, NAA 0.2 mg/L, sucrose 3%, and agar 4.5‰; and the rooting medium had a pH value of 5.7.

Example 2

This example provided a tissue culture method similar to that in Example 1, the only difference was that: the proliferation medium used the DCR medium as a basic medium, and only included the following components: 6-BA 1.5 mg/L, NAA 0.6 mg/L, sucrose 3%, and agar 4.5‰.

Example 3

This example provided a tissue culture method similar to that in Example 1, the difference was that: the induction medium used a P6 medium as a basic medium; and the proliferation medium used the DCR medium as a basic medium, and only included the following components: 6-BA 1 mg/L, NAA 0.4 mg/L, sucrose 3%, and agar 4.5‰.

Example 4

A propagation method of *Cathaya argyrophylla* included the following steps: the tissue culture seedling obtained in Example 1 was subjected to domestication indoors for 2 weeks; the tissue culture seedling was taken out from a medium, washed with sterile water, and planted into a culture substrate (including peat and perlite at a volume ratio of 4:1) to obtain a tissue culture seedling of a clone of the *Cathaya argyrophylla*.

Example 5

A propagation method of *Cathaya argyrophylla* included the following steps: the tissue culture seedling obtained in Example 2 was subjected to domestication indoors for 2 weeks; the tissue culture seedling was taken out from a medium, washed with sterile water, and planted into a culture substrate (including peat and perlite at a volume ratio of 4:1) to obtain a tissue culture seedling of a clone of the *Cathaya argyrophylla*.

Example 6

A propagation method of *Cathaya argyrophylla* included the following steps: the tissue culture seedling obtained in Example 3 was subjected to domestication indoors for 2 weeks; the tissue culture seedling was taken out from a medium, washed with sterile water, and planted into a culture substrate (including peat and perlite at a volume ratio of 4:1) to obtain a tissue culture seedling of a clone of the *Cathaya argyrophylla*.

Application Example 1

Screening of most suitable medium for each stage of tissue culture in *Cathaya argyrophylla*

Experimental Materials

*Cathaya argyrophylla* seeds were collected from Guangxi Jinxiu *Cathaya argyrophylla* Conservation Station and Huaping National Nature Reserve on Oct. 25 and Oct. 27, 2020, respectively. The seeds were sealed and refrigerated in a refrigerator at 5° C. for 4 weeks. A mature zygotic embryo of *Cathaya argyrophylla* was taken as an explant.

Experimental Method

Seeds from both sites were tested in a same manner as follows:

Washing, Surface Sterilization, and Inoculation of Explant

The seeds were peeled off from cones of *Cathaya argyrophylla*, rinsed with tap water, seed coat was sterilized with a 0.1% $KMnO_4$ solution for 20 min to 30 min, and the seed coat was peeled off on an ultra-clean workbench to obtain peeled seeds; the peeled seeds were put into 70% alcohol for 30 s, sterilized in 0.1% mercuric chloride for 5 min to 6 min, rinsed 4 to 5 times with sterile water. A seed embryo was taken out from the peeled seeds with a scalpel under aseptic conditions and inoculated horizontally into a medium. 1 seed embryo was placed in each bottle. 60 bottles were inoculated for each treatment, repeated 3 times.

Induction of Callus and Adventitious Bud

In this trial, 1/2MS, P6, and DCR each were used as a basic medium, and then added with 1.0, and 1.5 $mg \cdot L^{-1}$ of 6-BA, respectively; a mature embryo of *Cathaya argyrophylla* was used as an explant. This trial was conducted with a completely randomized design. A suitable medium and a concentration of 6-BA for adventitious bud induction of mature embryos of *Cathaya argyrophylla* were determined. The induction culture of adventitious buds was conducted for a total of 10 weeks.

Proliferation and Domestication of Adventitious Bud

The adventitious bud of *Cathaya argyrophylla* induced by the 1/2MS medium was used as an explant, and then the 1/2MS medium was used as a basic medium, and 0.5 $mg \cdot L^{-1}$ of 6-BA and 0.2, 0.4, and 0.6 mg·$L^{-1}$ of NAA were added separately for proliferation and domestication of the adventitious bud.

The adventitious bud of *Cathaya argyrophylla* induced by the P6 medium was used as an explant, and then the P6 medium was used as a basic medium, and 0.5 mg·$L^{-1}$ of 6-BA and 0.2, and 0.6 mg·$L^{-1}$ of NAA were added separately for proliferation and domestication of the adventitious bud.

The adventitious bud of *Cathaya argyrophylla* induced by the DCR medium was used as an explant, and then the DCR medium was used as a basic medium, and 0.5 mg·$L^{-1}$ of 6-BA and 0.4, and 0.6 mg·$L^{-1}$ of AA were added separately for proliferation and domestication of the adventitious bud.

The proliferation and domestication of adventitious bud were conducted for 12 weeks.

Induction of Roots for Adventitious Bud

The adventitious bud that was subjected to proliferation and domestication on the 1/2MS medium was transferred to 1/2MS+0.1% AC to allow culture for 3 weeks, transferred to the 1/2MS medium to allow culture for 4 weeks, and then transferred to the 1/2MS medium separately added with 0.5, 1.0, 1.5 of IBA and 0.2 mg·$L^{-1}$ of NAA to allow culture for 8 weeks.

The adventitious bud that was subjected to proliferation and domestication on the P6 medium was transferred to P6+0.1% AC to allow culture for 3 weeks, transferred to the P6 medium to allow culture for 4 weeks, and then transferred to the P6 medium separately added with 0.5, 1.0, 1.5 of IBA and 0.2 mg·$L^{-1}$ of NAA to allow culture for 8 weeks.

The adventitious bud that was subjected to proliferation and domestication on the DCR medium was transferred to DCR+0.1% AC to allow culture for 3 weeks, transferred to the DCR medium to allow culture for 4 weeks, and then transferred to the DCR medium separately added with 0.5, 1.0, 1.5 of IBA and 0.2 mg·$L^{-1}$ of NAA to allow culture for 8 weeks.

Addition and Preparation of Medium

All media were supplemented with 30 g·$kg^{-1}$ sucrose, 4.5 g·$kg^{-1}$ agar, with pH=5.6-5.8. The phytohormones were added to the medium before sterilization at 121° C.

Culture Conditions

The culture was conducted at (25±2)° C., with sufficient illumination for (12-14) h per day at a light intensity of (2,000-3,000) 1×. A culture room had a relative humidity of 60% to 80%.

Statistical Indicator

Number of calluses=number of explants that produced callus

Callus rate=number of explants producing callus/total number of explants in this treatment×100%

Number of induced buds=number of explants producing adventitious buds

Bud induction rate=number of explants producing adventitious buds/total number of explants in this treatment×100%

Number of proliferation=number of explants that proliferated

Proliferation rate=number of explants that proliferated/total number of explants in this treatment×100%

Number of rooting=number of explants that produced adventitious roots

Rooting rate=number of explants producing adventitious roots/total number of explants in this treatment×100%

All experimental designs were statistically analyzed using SPSS 20.0 software. All experiments were analyzed by analysis of variance and Duncan's significant difference test.

Effects of Basic Medium and Growth Regulators on Induction of Adventitious Buds From Mature Embryos of *Cathaya argyrophylla*

Effect of Medium on Callus and Adventitious Bud Induction of Mature Embryos of *Cathaya argyrophylla*

TABLE 1

Callus and adventitious buds induced by *Cathaya argyrophylla* seeds in Jinxiu at different cultures and concentrations

| Indicator | Hormone and concentration (mg/L) 6-BA | Medium 1/2MS | DCR | P6 |
|---|---|---|---|---|
| Callus rate | 0.5 | 15.56 ± 8.68ab | 14.81 ± 14.81ab | 59.72 ± 14.50c |
| | 1.0 | 30.16 ± 8.40abc | 8.93 ± 4.49a | 36.62 ± 16.14abc |
| | 1.5 | 23.61 ± 11.87abc | 0.00 ± 0.00a | 50.07 ± 17.71bc |
| Induction rate of adventitious bud | 0.5 | 37.78 ± 6.19ab | 42.96 ± 12.92ab | 28.24 ± 16.44a |
| | 1.0 | 30.16 ± 8.40ab | 48.21 ± 5.74ab | 29.08 ± 15.90ab |
| | 1.5 | 29.167 ± 18.16ab | 73.33 ± 6.67b | 32.15 ± 18.91ab |
| Withering rate | 0.5 | 0.00 ± 0.00a | 0.00 ± 0.00a | 0.00 ± 0.00a |
| | 1.0 | 0.00 ± 0.00a | 0.00 ± 0.00a | 5.80 ± 2.90a |
| | 1.5 | 11.11 ± 11.11a | 0.00 ± 0.00a | 5.93 ± 1.58a |
| Non-developmental rate | 0.5 | 46.67 ± 3.33c | 42.22 ± 8.89bc | 12.04 ± 6.48a |
| | 1.0 | 39.68 ± 3.18bc | 42.86 ± 7.14bc | 28.50 ± 2.41ab |
| | 1.5 | 36.11 ± 1.39bc | 26.67 ± 6.67ab | 11.86 ± 3.16a |

As shown in Table 1, among the three media 1/2MS, DCR, and P6, the P6 medium added with 0.5 mg/L 6-BA had a significant maximum callus rate of 59.72%. When 1.0 mg/L and 0.5 mg/L of 6-BA were added to 1/2MS and DCR medium, the maximum callus rates were 30.16% and 14.81%, respectively.

Adventitious buds were induced in the 3 media of 1/2MS, DCR, and P6 with different concentrations of 6-BA growth regulator, and their adventitious bud induction rates were significantly different. When 1.5 mg/L 6-BA was added to the DCR and P6 media, the induction rates of adventitious buds reached maximum, which were 73.33% and 32.15%, respectively. When 0.5 mg/L 6-BA was added to the 1/2MS medium, the adventitious bud induction rate reached a maximum of 37.78%.

Withering occurred mainly for the withering of germinated seeds, partial withering of callus, and withering of adventitious buds. The callus and adventitious buds of *Cathaya argyrophylla* seeds from Jinxiu had the highest withering rate when adding different concentrations of 6-BA: when adding 1.5 mg/L of 6-BA on 1/2MS medium, the withering rate was 11.11%; when 0.5 mg/L of 6-BA and 1.0 mg/L of 6-BA were added, the withering rate was 0. The withering rate of DCR medium added with different concentrations of 6-BA was 0. On the P6 medium, when 0.5 mg/L of 6-BA was added, the withering rate was 0; at 1.0 mg/L and 1.5 mg/L of 6-BA, the withering rates were 5.80% and 5.93%, respectively. However, there was no significant difference in the withering rates of P6, DCR, and 1/2MS with different concentrations of 6-BA.

The undeveloped situation was mainly due to the stagnation of *Cathaya argyrophylla* seeds after germination. When different concentrations of 6-BA were added to the 3 media of P6, DCR, and 1/2MS, there were significant differences in development stagnation of seeds. On the P6 medium, the non-developmental rates of 0.5 mg/L 6-BA and 1.5 mg/L 6-BA were significantly lower, being 12.04% and 11.86%, respectively. When the 1/2MS medium was supplemented with 0.5 mg/L 6-BA, the non-developmental rate was 46.67% and was significantly the largest. When different concentrations of 6-BA were added to the DCR medium, the non-developmental rate of seeds was between those of the P6 and 1/2MS media.

concentration, the induction rate of *Cathaya argyrophylla* callus gradually decreased. An average induction rate of adventitious buds was 30% in Jinxiu provenance and 51% in Guilin provenance. When the concentration of 6-BA was 1.5 mg/L, the induction rate of adventitious buds was 32.15% in Jinxiu provenance and 69.22% in Guilin provenance. With an increase of the 6-BA concentration, the induction rate of *Cathaya argyrophylla* adventitious buds gradually increased.

An average induction rate of callus on 1/2MS medium was 23% in Jinxiu provenance and 55% in Guilin provenance. When the concentration of 6-BA was 1.0 mg/L, the induction rate was 30.16% in Jinxiu provenance and 60.32% in Guilin provenance. With an increase of the 6-BA concentration, the induction rate of *Cathaya argyrophylla* callus decreased. An average induction rate of adventitious buds was 32% in Jinxiu provenance and 24% in Guilin provenance. When the concentration of 6-BA was 0.5 mg/L, the maximum induction rate was 37.78% in Jinxiu provenance and 25.00% in Guilin provenance (25.40% at 1.0 mg/L). With an increase of the 6-BA concentration, the induction rate of *Cathaya argyrophylla* adventitious buds decreased.

TABLE 2

Callus and adventitious buds induced by *Cathaya argyrophylla* seeds in Guilin at different cultures and concentrations

| Indicator | Hormone and concentration (mg/L) 6-BA | Medium 1/2MS | DCR | P6 |
|---|---|---|---|---|
| Callus rate | 0.5 | 47.22 ± 23.73a | 66.48 ± 11.11a | 24.61 ± 4.45a |
| | 1.0 | 60.32 ± 24.95a | 20.83 ± 4.17a | 9.78 ± 7.71a |
| | 1.5 | 58.33 ± 30.05a | 43.33 ± 23.33a | 13.73 ± 2.29a |
| Induction rate of adventitious bud | 0.5 | 25.00 ± 14.43ab | 7.41 ± 7.41a | 39.89 ± 10.63ab |
| | 1.0 | 25.40 ± 12.99ab | 45.83 ± 4.17ab | 45.29 ± 10.62ab |
| | 1.5 | 20.83 ± 20.83a | 26.67 ± 26.67ab | 69.22 ± 1.38b |
| Withering rate | 0.5 | 0.00 ± 0.00a | 0.00 ± 0.00a | 3.53 ± 1.85ab |
| | 1.0 | 0.00 ± 0.00a | 16.67 ± 8.33b | 2.90 ± 2.90a |
| | 1.5 | 8.33 ± 8.33ab | 0.00 ± 0.00a | 4.62 ± 0.14ab |
| Non-developmental rate | 0.5 | 27.78 ± 14.70a | 26.11 ± 3.89a | 30.93 ± 12.69a |
| | 1.0 | 14.29 ± 14.29a | 16.67 ± 16.67a | 42.03 ± 7.97a |
| | 1.5 | 12.50 ± 12.50a | 30.00 ± 10.00a | 7.66 ± 4.16a |

As shown in Table 2, when the callus and adventitious buds of *Cathaya argyrophylla* seeds derived from Guilin were induced: when 1.0 mg/L 6-BA was added to the DCR medium, the withering rate was significantly maximum at 16.67%. When adding 0.5 mg/L and 1.5 mg/L 6-BA on the DCR medium, and adding 0.5 mg/L and 1.0 mg/L 6-BA on the 1/2MS medium, the withering rate was significantly minimum at 0. When the *Cathaya argyrophylla* seeds derived from Guilin were inducing callus and adventitious buds: the maximum seed non-developmental rate was 42.03% when 1.0 mg/L 6-BA was added to the P6 medium; the minimum seed non-developmental rate was at 7.66% when 1.5 mg/L 6-BA was added to the P6 medium. There was no significant difference in the non-developmental rate of *Cathaya argyrophylla* seeds derived from Guilin when callus and adventitious buds were induced when different concentrations of 6-BA were added to P6, ½MS, and DCR3 media.

An average induction rate of callus on P6 medium was 49% in Jinxiu provenance and 16% in Guilin provenance. When the concentration of 6-BA was 0.5, the maximum callus induction rate was 59.72% in Jinxiu provenance and 24.61% in Guilin provenance. With an increase of the 6-BA An average induction rate of adventitious buds on the DCR medium was 55% in Jinxiu provenance and 27% in Guilin provenance. When the concentration of 6-BA was 1.5 mg/L, the maximum induction rate was 73.33% in Jinxiu provenance. With an increase of the 6-BA concentration, the induction rate of *Cathaya argyrophylla* adventitious buds increased gradually. When the concentration of 6-BA was 1.0 mg/L, the maximum induction rate was 45.83% in Guilin provenance. With an increase of the 6-BA concentration, the induction rate of *Cathaya argyrophylla* adventitious buds decreased gradually.

Different media and hormone concentrations caused significant differences in the induction rate of mature embryo callus of *Cathaya argyrophylla*: in the 3 media of 1/2MS, DCR, and P6, the induction rate of DCR to callus was significantly the lowest; the callus induction rate on P6 medium was significantly the highest; and the 1/2MS was between 1/2MS and P6 media.

On the DCR medium, as the concentration of the growth regulator increased, the callus induction rate gradually decreased, even to 0%. On the P6 medium, the callus induction rate was the most significant, which was 59.72% when a low concentration of growth regulator was added.

There was also a higher callus induction rate (50.7%) on the P6 medium added with high concentration of growth regulators. On the 1/2MS medium, the callus was induced by adding different concentrations of growth regulators; the callus induction rate increased and then decreased with the increase of concentration (0.5 mg/L, 1.0 mg/L, and 1.5 mg/L); the callus induction rate was 30.16%, as the highest value when the concentration of 6-BA was 1.0 mg/L. There was no significant difference in callus withering rate or adventitious bud withering rate.

Effects of Concentration Combinations of Growth Regulators on Proliferation and Domestication of adventitious Buds Effects of Media and Growth Regulators on Proliferation and Domestication of *Cathaya argyrophylla*

TABLE 3

Domestication of *Cathaya argyrophylla* seeds in Jinxiu at different cultures and concentrations

| | Hormone and concentration (mg/L) | | Medium | | |
|---|---|---|---|---|---|
| Indicator | 6-BA | NAA | 1/2MS | DCR | P6 |
| Callus | 0.5 | 0.2 | 100.00 ± 0.00e | 31.94 ± 9.11ab | 71.77 ± 9.05de |
| | 1.0 | 0.4 | 60.92 ± 8.57bcd | 57.77 ± 11.28bcd | 33.63 ± 11.25abc |
| | 1.5 | 0.6 | 66.67 ± 16.67cd | 12.26 ± 6.57a | 48.96 ± 12.20bcd |
| Proliferated adventitious bud | 0.5 | 0.2 | 0.00 ± 0.00a | 50.28 ± 0.28e | 12.33 ± 2.26abc |
| | 1.0 | 0.4 | 6.10 ± 0.51ab | 23.72 ± 1.89bcd | 14.13 ± 1.30abc |
| | 1.5 | 0.6 | 33.33 ± 16.67de | 46.23 ± 2.07e | 24.85 ± 0.77cd |
| Withering | 0.5 | 0.2 | 0.00 ± 0.00a | 17.78 ± 8.94ab | 15.90 ± 8.25ab |
| | 1.0 | 0.4 | 24.03 ± 1.51b | 12.90 ± 7.23ab | 8.86 ± 4.44ab |
| | 1.5 | 0.6 | 0.00 ± 0.00a | 21.15 ± 3.44ab | 21.03 ± 14.30ab |
| Non-development | 0.5 | 0.2 | 0.00 ± 0.00a | 0.00 ± 0.00a | 0.00 ± 0.00a |
| | 1.0 | 0.4 | 0.00 ± 0.00a | 5.61 ± 5.61ab | 43.39 ± 13.76b |
| | 1.5 | 0.6 | 0.00 ± 0.00a | 20.36 ± 6.51ab | 5.16 ± 2.60ab |

As shown in Table 3, during the multiplication and domestication, the *Cathaya argyrophylla* seeds of Jinxiu provenance had a significantly higher callus rate when 0.5 mg/L of 6-BA and 0.2 mg/L of NAA were added to 1/2MS and P6 media, which were 100% and 71.77%, respectively. When 0.5 mg/L of 6-BA and 0.2 mg/L of NAA were added to the DCR medium, the callus rate of callus in 1/2MS medium was significantly lower at 12.26%. When 0.5 mg/L of 6-BA and 0.2 mg/L of NAA and 1.5 mg/L of 6-BA and 0.6 mg/L of NAA were added to the DCR medium, the proliferation rate of adventitious buds was significantly higher, being 50.28% and 46.23%, respectively. When 0.5 mg/L of 6-BA and 0.2 mg/L of NAA were added to the 1/2MS medium, the proliferation rate of adventitious buds was significantly lowest at 0.00%. When 0.5 mg/L of 6-BA and 0.2 mg/L of NAA, and 1.5 mg/L of 6-BA and 0.6 mg/L of NAA were added to 1/2MS medium, the withering rate was significantly lowest at 0.00%. When 1.0 mg/L of 6-BA and 0.4 mg/L of NAA were added to 1/2MS medium, the withering rate was significantly maximum at 24.03%. When adding 0.5 mg/L of 6-BA and 0.2 mg/L of NAA on 1/2MS, DCR, P6 media, and adding 1.0 mg/L of 6-BA and 0.4 mg/L of NAA, and 1.5 mg/L of 6-BA and 0.6 mg/L of NAA to 1/2MS medium, the withering rate was significantly lowest at 0.00%. When 0.5 mg/L of 6-BA and 0.2 mg/L of NAA were added to the P6 medium, the non-developmental rate was significantly the lowest. When 1.0 mg/L of 6-BA and 0.4 mg/L of NAA were added to the P6 medium, the non-developmental rate was significantly the highest at 43.39%.

TABLE 4

Domestication of *Cathaya argyrophylla* seeds in Guilin at different cultures and concentrations

| | Hormone and concentration (mg/L) | | Medium | | |
|---|---|---|---|---|---|
| Indicator | 6-BA | NAA | 1/2MS | DCR | P6 |
| Callus | 0.5 | 0.2 | 100.00 ± 0.00c | 25.00 ± 0.00b | 86.67 ± 6.67c |
| | 1.0 | 0.4 | 0.00 ± 0.00a | 10.00 ± 0.00ab | 25.00 ± 0.00b |
| | 1.5 | 0.6 | 0.00 ± 0.00a | 14.76 ± 8.66ab | 16.67 ± 16.67ab |
| Proliferated adventitious bud | 0.5 | 0.2 | 0.00 ± 0.00a | 35.00 ± 0.00c | 0.00 ± 0.00a |
| | 1.0 | 0.4 | 20.00 ± 0.00b | 55.00 ± 0.00f | 0.00 ± 0.00a |
| | 1.5 | 0.6 | 0.00 ± 0.00a | 44.84 ± 2.60d | 48.89 ± 0.56e |
| Withering | 0.5 | 0.2 | 0.00 ± 0.00a | 40.00 ± 0.00abcd | 13.33 ± 6.67a |
| | 1.0 | 0.4 | 80.00 ± 0.00d | 35.00 ± 0.00abc | 75.00 ± 0.00cd |
| | 1.5 | 0.6 | 66.67 ± 33.33bcd | 23.37 ± 11.30ab | 34.45 ± 17.22abc |

TABLE 4-continued

Domestication of *Cathaya argyrophylla* seeds in Guilin at different cultures and concentrations

| | Hormone and concentration (mg/L) | | Medium | | |
|---|---|---|---|---|---|
| Indicator | 6-BA | NAA | 1/2MS | DCR | P6 |
| Non-development | 0.5 | 0.2 | 0.00 ± 0.00a | 0.00 ± 0.00a | 0.00 ± 0.00a |
| | 1.0 | 0.4 | 0.00 ± 0.00a | 0.00 ± 0.00a | 0.00 ± 0.00a |
| | 1.5 | 0.6 | 33.33 ± 33.33a | 17.02 ± 5.82a | 0.00 ± 0.00a |

As shown in Table 4, during the multiplication and domestication, the *Cathaya argyrophylla* seeds of Guilin provenance had a significantly higher callus rate when 0.5 mg/L of 6-BA and 0.2 mg/L of NAA were added to 1/2MS and P6 media, which were 100% and 86.67%, respectively. However, when 1.0 mg/L of 6-BA and 0.4 mg/L of NAA, and 1.5 mg/L of 6-BA and 0.6 mg/L of NAA were added to the 1/2MS medium, the callus rate was significantly lowest at 0.00%.

When 1.0 mg/L of 6-BA and 0.4 mg/L of NAA were added to the DCR medium, the proliferation rate of adventitious buds was significantly maximum at 55.00%. When 0.5 mg/L of 6-BA and 0.2 mg/L of NAA, and 1.50 mg/L of 6-BA and 0.64 mg/L of NAA were added to the 1/2MS, as well as 0.5 mg/L of 6-BA and 0.2 mg/L of NAA, and 1.0 mg/L of 6-BA and 0.4 mg/L of NAA were added to the P6 medium, the induction rate of adventitious buds was significantly lowest at 0.00%.

When 1.0 mg/L 6-BA and 0.4 mg/L NAA were added to 1/2MS medium, the withering rate was significantly maximum at 80.00%. However, when 0.5 mg/L 6-BA and 0.2 mg/L NAA were added, the withering rate was significantly minimum at 0.00%.

The 3 mediums P6, DCR, and 1/2MS and different concentrations of 6-BA and NAA had no significant effect on the non-developmental rate.

Effects of Concentration Combinations of Growth Regulator on Adventitious Root Induction

TABLE 5

Effects of different media and growth regulators on rooting of adventitious buds for *Cathaya argyrophylla* seeds in Jinxiu

| Hormone and concentration (mg/L) | | Medium | | |
|---|---|---|---|---|
| IBA | NAA | DCR | 1/2MS | P6 |
| 0.50 | 0.2 | 0.00 ± 0.00a | 16.67 ± 8.33b | 1.04 ± 1.04a |
| 1.00 | 0.2 | 0.00 ± 0.00a | 0.00 ± 0.00a | 0.00 ± 0.00a |
| 1.50 | 0.2 | 0.00 ± 0.00a | 0.00 ± 0.00a | 4.76 ± 4.76a |

As shown in Table 5, the average induction rate of adventitious root induction of adventitious buds of *Cathaya argyrophylla* derived from Jinxiu provenance was 0.00% on DCR medium, which was significantly the lowest. After adding different concentrations of growth regulators IBA and NAA, no adventitious roots were induced within an experimental design time. An average induction rate on P6 medium was 1.93%. When the concentration of NAA added was 0.2 mg/L, the induction rate of adventitious roots of *Cathaya argyrophylla* decreased and then increased with an increase of the IBA concentration. When the IBA concentration was 1.5 mg/L, the maximum induction rate was 4.76%. An average induction rate on 1/2MS medium was 5.56%. When the concentration of NAA was 0.2 mg/L and the concentration of IBA was 0.5 mg/L, the induction rate of adventitious roots was significantly maximum at 16.67%. With an increase of the concentrations of IBA and NAA, the callus of *Cathaya argyrophylla* was reduced, and no adventitious root was induced, showing that the induction rate was 0.00%.

TABLE 6

Effects of different media and growth regulators on rooting of adventitious buds for *Cathaya argyrophylla* seeds in Guilin

| Treatment with growth regulator (mg/L) | | Medium | | |
|---|---|---|---|---|
| IBA | NAA | DCR | 1/2MS | P6 |
| 0.50 | 0.2 | 0.00 ± 0.00a | 21.43 ± 3.57b | 1.04 ± 1.04a |
| 1.00 | 0.2 | 0.00 ± 0.00a | 0.00 ± 0.00a | 0.00 ± 0.00a |
| 1.50 | 0.2 | 0.00 ± 0.00a | 0.00 ± 0.00a | 4.76 ± 4.76a |

As shown in Table 6, the average induction rate of adventitious root induction of adventitious buds of *Cathaya argyrophylla* derived from Guilin provenance was 0.00% on DCR medium, which was significantly the lowest. After adding different concentrations of growth regulators IBA and NAA, no adventitious roots were induced within an experimental design time. An average induction rate of the callus on P6 medium was 1.93%. When the concentration of NAA added was 0.2 mg/L, the induction rate of adventitious roots of *Cathaya argyrophylla* decreased and then increased with an increase of the IBA concentration. When the IBA concentration was 1.5 mg/L, the maximum induction rate was 4.76%. An average induction rate of the callus on 1/2MS medium was 7.14%. When the concentration of NAA was 0.2 mg/L and the concentration of IBA was 0.5 mg/L, the induction rate of adventitious roots was significantly maximum at 21.43%. With an increase of the concentrations of IBA and NAA, the callus of *Cathaya argyrophylla* was reduced, and no adventitious root was induced, showing that the induction rate was 0.00%.

In summary, the induction rate of callus from Jinxiu (P6 medium) and Guilin (DCR medium) provenances was the highest when 0.5 mg/L 6-BA was added to induce callus from seed embryos. Jinxiu (DCR) and Guilin (P6) had the highest adventitious bud induction rate when 1.5 mg/L 6-BA was added. In the stage of adventitious bud proliferation, when adventitious bud induction from Jinxiu and Guilin provenances (both on DCR medium) were conducted with 0.5 mg/L 6-BA and 0.2 mg/L NAA, and 1.0 mg/L 6-BA and 0.4 mg/L NAA, respectively, the proliferation and domestication rate of adventitious buds were the highest. Similarly, when the adventitious buds of Jinxiu and Guilin provenances after multiplication and domestication were added with low concentrations of 0.5 mg/L IBA and 0.2 mg/L NAA growth regulators on 1/2MS medium, the adventitious root induction rate of adventitious buds was the highest.

Although the present disclosure has been set forth as above in preferred examples, they are not intended to limit the present disclosure. Those skilled in the art can make various alterations and modifications without departing from the spirit and scope of the present disclosure. Therefore, the protection scope of the present disclosure should be subject to the protection scope defined by the claims.

The invention claimed is:

1. A tissue culture method of *Cathaya argyrophylla*, comprising the following steps:

inoculating an explant of the *Cathaya argyrophylla* into an induction medium to allow induction culture to obtain an adventitious bud of the *Cathaya argyrophylla*; wherein the explant comprises a zygotic embryo; the explant is derived from *Cathaya argyrophylla* in Jinxiu Yao Autonomous County of Guangxi or Huaping Town in Guilin;

the induction medium comprises a basic medium and 1.5 mg/L of 6-benzyladenine (6-BA); and the basic medium of the induction culture is selected from the group consisting of a DCR medium and a P6 medium;

inoculating the adventitious bud of the *Cathaya argyrophylla* into a proliferation medium to allow proliferation culture to obtain a proliferated adventitious bud; wherein when the explant is derived from the *Cathaya argyrophylla* in the Jinxiu Yao Autonomous County of Guangxi, the proliferation medium uses the DCR medium as a basic medium, and further comprises 0.5 mg/L of the 6-BA and 0.2 mg/L of 1-naphthylacetic acid (NAA); alternatively, the proliferation medium uses the DCR medium as a basic medium, and further comprises 1.5 mg/L of the 6-BA and 0.6 mg/L of the NAA; and when the explant is derived from the *Cathaya argyrophylla* in the Huaping Town in Guilin, the proliferation medium uses the DCR medium as a basic medium, and further comprises 1 mg/L of the 6-BA and 0.4 mg/L of the NAA;

inoculating the proliferated adventitious bud into a rooting medium to allow rooting culture to obtain a tissue culture seedling;

wherein:

the rooting medium uses a 1/2 MS medium as a basic medium, and further comprises 0.5 mg/L of indole-3-butyric acid (IBA) and 0.2 mg/L of the NAA; and the induction medium, the proliferation medium, and the rooting medium each further comprise the following components in mass percentage: 3% of sucrose and 4.5% % of agar.

2. The tissue culture method according to claim 1, wherein the induction medium, the proliferation medium, and the rooting medium each have a pH value of 5.6 to 5.8.

3. The tissue culture method according to claim 1, wherein the induction culture, the proliferation culture, and the rooting culture are independently conducted by: a culture temperature of 23° C. to 27° C., a daily illumination time of 12 h to 14 h, a light intensity of 2,000 1× to 3,000 1×, and a relative humidity of 60% to 80%.

4. The tissue culture method according to claim 1, wherein the induction culture is conducted for 10 weeks; the proliferation culture is conducted for 12 weeks; and the rooting culture is conducted for 8 weeks.

5. A propagation method of *Cathaya argyrophylla*, comprising the following steps:

preparing a tissue culture seedling by the tissue culture method according to claim 1; and subjecting the tissue culture seedling to transplanting culture to obtain a *Cathaya argyrophylla* seedling.

6. The propagation method according to claim 5, wherein the induction medium, the proliferation medium, and the rooting medium each have a pH value of 5.6 to 5.8.

7. The propagation method according to claim 5, wherein the induction culture, the proliferation culture, and the rooting culture are independently conducted by: a culture temperature of 23° C. to 27° C., a daily illumination time of 12 h to 14 h, a light intensity of 2,000 1× to 3,000 1×, and a relative humidity of 60% to 80%.

8. The propagation method according to claim 5, wherein the induction culture is conducted for 10 weeks; the proliferation culture is conducted for 12 weeks; and the rooting culture is conducted for 8 weeks.

9. The propagation method according to claim 5, wherein a culture substrate of the transplanting culture comprises peat and perlite; and the peat and the perlite in the culture substrate are at a volume ratio of 4:1.

10. The propagation method according to claim 6, wherein a culture substrate of the transplanting culture comprises peat and perlite; and the peat and the perlite in the culture substrate are at a volume ratio of 4:1.

* * * * *